United States Patent
Al-Zaydi et al.

(10) Patent No.: US 11,492,362 B1
(45) Date of Patent: Nov. 8, 2022

(54) PYRIDINE DERIVATIVES FOR THE TREATMENT OF HYPERPROLIFERATIVE DISEASES

(71) Applicant: King Abdulaziz University, Jeddah (SA)

(72) Inventors: Khadijah M. Al-Zaydi, Jeddah (SA); Meaad Bagazi, Jeddah (SA); Tamer Said Saleh, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 17/673,853

(22) Filed: Feb. 17, 2022

(51) Int. Cl.
| | |
|---|---|
| *C07D 519/00* | (2006.01) |
| *C07D 409/12* | (2006.01) |
| *A61P 35/00* | (2006.01) |
| *A61P 35/02* | (2006.01) |

(52) U.S. Cl.
CPC ............ *C07D 519/00* (2013.01); *A61P 35/00* (2018.01); *A61P 35/02* (2018.01); *C07D 409/12* (2013.01)

(58) Field of Classification Search
CPC ....................................................... A61P 35/00
See application file for complete search history.

(56) References Cited

U.S. PATENT DOCUMENTS

| | | | |
|---|---|---|---|
| 9,200,000 | B2 | 12/2015 | Helal et al. |
| 2007/0299103 | A1 | 12/2007 | Abel et al. |
| 2011/0077248 | A1 | 3/2011 | Vu et al. |

OTHER PUBLICATIONS

Abd El Baset Hassanien, et al., 2,6-Bis[3-N,N-dimethylamino-1-oxopropen-1-yl]pyridine as a building block in heterocyclic synthesis : synthesis of 2,2':6',2"-terpyridines and 2,6-bis[pyrazolyl, isoxazolyl, diazepinyl, pyrazolo[5,1-a]pyrimidinyl and pyrazolo- (Year: 2004).*
Continued from U above [4,3-d]pyridazinyl]pyridines, J. of Chem. Res. J. of Chem. Res. 536-540 (2004). (Year: 2004).*
Bagazi et al., "A Novel Studies of Dienaminone: Synthesis of Heterocyclic Compounds Using Green Chemistry Methods", EAMHC-2019, Sep. 15, 2019.
Behbehani et al., "Ultrasound-assisted regio- and stereoselective synthesis of bis-[1',4'-diaryl-1-oxo-spiro-benzosuberane-2,5'-pyrazoline] derivatives via 1,3-dipolar cycloaddition", RSC Advances, Issue 33, 25642-25649, Mar. 4, 2015.
Zeid et al., "2, 6-Bis [3-N,N-dimethylamino-1-oxopropen-1-yl]pyridine as a building block in heterocyclic synthesis synthesis of 2,2',6',2"-terpyridines and 2,6-bis[pyrazolyl, isoxazolyl, diazepinyl, pyrazolo[5,1-a]pyrimidinyl and pyrazolo-[4,3-d]pyridazinyl]pyridines", Journal of Chemical Research, 536-540, Aug. 2004.
Ibrahim et al., "The first Q-Tube based high-pressure synthesis of anti-cancer active thiazolo[4,5-c]pyridazines via the [4 + 2] cyclocondensation of 3-oxo-2-arylhydrazonopropanals with 4-thiazolidinones", Scientific Reports (2020) 10:6492.
Mittersteiner et al., "Ultrasound-assisted synthesis of pyrimidines and their fused derivatives: A review", Ultrasonics Sonochemistry 79, Jul. 27, 2021, 105683.

* cited by examiner

*Primary Examiner* — Erich A Leeser
(74) *Attorney, Agent, or Firm* — WC&F IP

(57) ABSTRACT

Methods of inducing apoptosis of cancer cells by contacting the cancer cells with a pyridine derivative are provided. Methods of treating a subject suffering from a hyperproliferative disease or complications thereof comprising the step of administering a therapeutically effective amount of a composition to the subject, wherein the composition comprises pyridine derivatives are provided.

6 Claims, 4 Drawing Sheets

PYRIDINE DERIVATIVES FOR THE TREATMENT OF HYPERPROLIFERATIVE DISEASES

FIELD OF THE INVENTION

The invention is generally related to disubstituted pyridine derivatives that enhance apoptosis and are useful for treating hyperproliferative diseases such as leukemia.

BACKGROUND OF THE INVENTION

Leukemia is a malignant tumor of the hematopoietic system and is a commonly diagnosed neoplasm that causes significant harm to human health and represents a significant cause of cancer-related deaths worldwide [1-7]. Leukemia accounts for almost 5% of all cancer cases ranking in sixth place among various human malignancies [4, 6]. Many types of leukemia are distinguished including acute myeloid leukemia (AML), a malignant blood disorder with a poor prognosis. The 5-year survival rate of an adult with AML is only about 50% or lower [8]. AML is generally characterized by the overproduction of myeloid blast cells that suffer from a blockage in their differentiation pathways, which leads to the crowding out of normal blood cells and platelets. The stages in which the differentiation of AML blast cells is arrested define the subtypes of AML (AML-M0 to M7). The clinical outcomes of patients with AML treated with available cytotoxic, targeted, and hematopoietic stem cell transplant therapy remains unsatisfactory with 3-8% survival at 5 years in patients aged 60 years and older and up to 50% in patients younger than 60 years of age [9-11]. This demonstrates an urgent need for the development of novel, efficacious, and well-tolerated therapeutic agents and strategies for the treatment of AML.

AML therapy is challenging because it is an extremely heterogeneous disease with various leukemogenic mutations and cytogenetic abnormalities with poorly understood interplay among them in each patient [12,13]. One solution to this issue may target a broader characteristic that is common among all AML cells but is sufficiently different from normal tissues. Growing evidence indicates that AML cells, compared to normal cells and irrespective of their genetic heterogeneity, have an increased susceptibility to the disruption of the balance between pro- and anti-oxidant forces [14]. On the other hand, the pyridine substructure is one of the most prevalent heterocycles found in natural products, pharmaceuticals, and functional materials [15]. In addition, some reports show potent cytotoxicity of bis pyridine alkaloids that were extracted from marine sources [16]. Other reports show that the structure activity relationship of non-fused pyridine systems that contains a bilateral basic chain and nitrogen heterocycles shows strong DNA binding and consequently induces the apoptosis of the cancer cells [17].

Novel cytotoxic agents useful for treating hyperproliferative diseases are needed.

SUMMARY

An aspect of the disclosure provides a method for inducing apoptosis of cancer cells comprising contacting the cancer cells with a pyridine derivative as described herein. In some embodiments, the cancer cells are leukemia cells.

Another aspect of the disclosure provides a method for treating a subject suffering from a hyperproliferative disease or complications thereof, comprising the step of administering a therapeutically effective amount of a composition to the subject, wherein the composition comprises a pyridine derivative as described herein. In some embodiments, the hyperproliferative disease is leukemia.

The foregoing and other objects, features, and advantages of the present disclosure will become more apparent from the following detailed description, which proceeds with reference to the accompanying figures.

DETAILED DESCRIPTION

Figure 1:
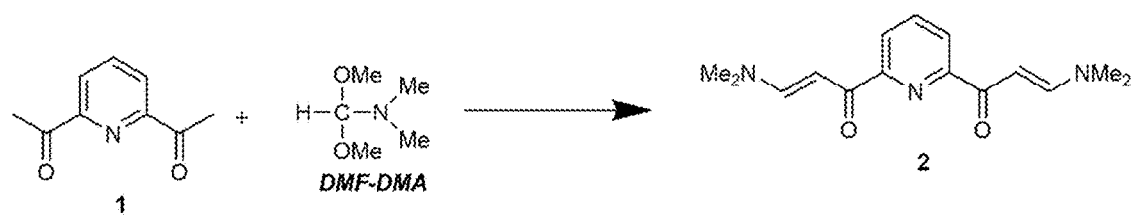
FIG. 1. Synthesis of compound 2.

Embodiments of the disclosure provide pyridine derivatives that induce apoptosis in cancer cells. Compositions containing these compounds are useful for treating cancer and complications thereof.

The disclosure provides dienaminone derivative compounds having a chemical structure of Formula I

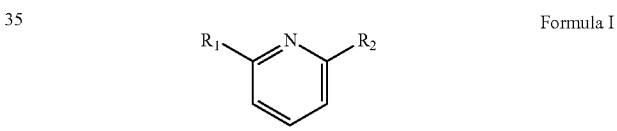

Formula I wherein $R_1$ is selected from the group consisting of

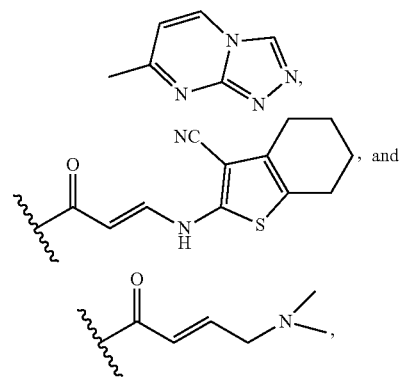

, and wherein $R_2$ is selected from the group consisting of

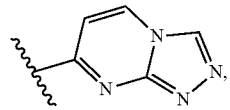

,

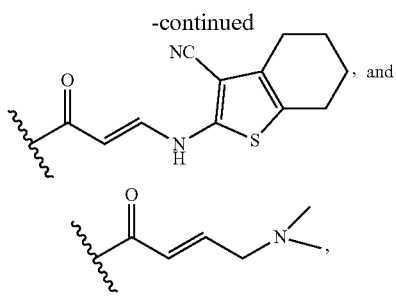

where $R_1$ and $R_2$ are independently the same or different.

In some embodiments, the compound has a chemical structure of Formula II

Formula II

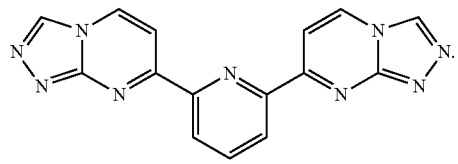

In some embodiments, the compound has a chemical structure of Formula III

Formula III

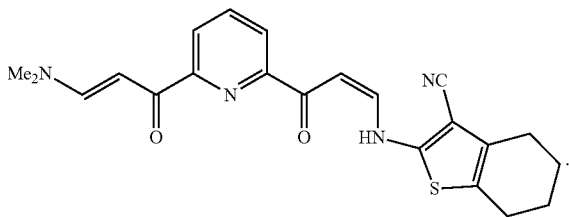

In some embodiments, the compound has a chemical structure of Formula IV

Formula IV

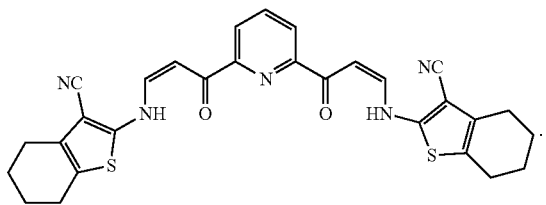

The compounds of the present disclosure can be in the form of a pharmaceutically acceptable salt or a solvate. The term "pharmaceutically acceptable salts" refers to salts prepared from pharmaceutically acceptable non-toxic bases or acids, including inorganic bases or acids and organic bases or acids. In case the compounds contain one or more acidic or basic groups, the disclosure also comprises their corresponding pharmaceutically or toxicologically acceptable salts, in particular their pharmaceutically utilizable salts. Thus, the compounds which contain acidic groups can be present on these groups and can be used according to the disclosure, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Compounds of the present disclosure which contain one or more basic groups, i.e. groups which can be protonated, can be present and can be used according to the disclosure in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds simultaneously contain acidic and basic groups in the molecule, the disclosure also includes, in addition to the salt forms mentioned, inner salts or betaines (zwitterions). The respective salts can be obtained by customary methods which are known to the person skilled in the art like, for example by contacting these with an organic or inorganic acid or base in a solvent or dispersant, or by anion exchange or cation exchange with other salts. The present disclosure also includes all salts of the compounds of the present disclosure which, owing to low physiological compatibility, are not directly suitable for use in pharmaceuticals but which can be used, for example, as intermediates for chemical reactions or for the preparation of pharmaceutically acceptable salts.

Furthermore, the present disclosure provides pharmaceutical compositions comprising a compound as described herein, or a prodrug compound thereof, or a pharmaceutically acceptable salt or solvate thereof as active ingredient together with a pharmaceutically acceptable carrier.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present disclosure encompass any composition made by admixing a compound as described herein and a pharmaceutically acceptable carrier.

The active agent may be combined with pharmaceutically acceptable excipients. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The compositions of the present disclosure may also contain other components such as, but not limited to, additives, adjuvants, buffers, tonicity agents, and preservatives. An additive such as a sugar, a glycerol, and other sugar alcohols, can be included in the compositions of the present disclosure. Pharmaceutical additives can be added to increase the efficacy or potency of other ingredients in the composition. For example, a pharmaceutical additive can be added to a composition of the present disclosure to improve the stability of the bioactive agent, to adjust the osmolality of the composition, to adjust the viscosity of the composition, or for another reason, such as effecting drug delivery. Non-limiting examples of pharmaceutical additives of the present disclosure include sugars, such as, saccharin trehalose, mannose, D-galactose, and lactose and flavorings such as orange oil.

In an embodiment, if a preservative is desired, the compositions may optionally be preserved with any well-known system such as benzyl alcohol with/without EDTA, benzalkonium chloride, chlorhexidine, Cosmocil® CQ, or Dowicil 200.

A pharmaceutical composition may additionally comprise one or more other compounds as active ingredients like one or more additional compounds of the present disclosure, a prodrug compound, other apoptosis inhibitors, or other anti-cancer or anti-tumor agents (e.g. chemotherapeutics) such as mitotic inhibitors, alkylating agents, antimetabolites, intercalating antibiotics, growth factor inhibitors, cell cycle inhibitors, enzyme inhibitors, topoisomerase inhibitors, biological response modifiers, antihormones, angiogenesis inhibitors, and anti-androgens. In some embodiments, the composition is administered with one or more of radiation therapy or immunotherapy.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

Another aspect of the disclosure provides a method of using the compounds as described herein as in vitro or in vivo cytotoxic agents. The disclosure also provides a compound as described herein under conditions sufficient to cause apoptosis of cancer cells.

In one embodiment, said compounds and pharmaceutical compositions are for the treatment of hyperproliferative diseases (i.e. cancer) such as brain, lung, squamous cell, skin, bladder, gastric, pancreatic, breast, head, neck, renal, kidney, ovarian, uterine, prostate, colorectal, esophageal, testicular, gynecological or thyroid cancer. In some embodiments, the pharmaceutical composition is for the treatment of blood cancer (i.e. chronic or acute leukemia). In another embodiment, said pharmaceutical composition is for the treatment of a noncancerous hyperproliferative disorder such as benign hyperplasia of the skin (e.g., psoriasis), restenosis, or prostate (e.g. benign prostatic hypertrophy (BPH)).

A patient or subject to be treated by any of the compositions or methods of the present disclosure can mean either a human or a non-human animal including, but not limited to dogs, horses, cats, rabbits, gerbils, hamsters, rodents, birds, aquatic mammals, cattle, pigs, camelids, and other zoological animals.

In some embodiments, the active agent is administered to the subject in a therapeutically effective amount. By a "therapeutically effective amount" is meant a sufficient amount of active agent to treat the disease or disorder at a reasonable benefit/risk ratio applicable to any medical treatment. It will be understood that the total daily usage of the compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific active agent employed; and like factors well known in the medical arts. For example, it is well within the skill of the art to start doses of the compound at levels or frequencies lower than those required to achieve the desired therapeutic effect and to gradually increase the dosage or frequency until the desired effect is achieved. However, the daily dosage of the active agent may be varied over a wide range from 0.01 to 1,000 mg per adult per day. In particular, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, in particular from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

The present disclosure provides a method of synthesizing dienaminone and its derivatives by using a pressurized reactor system (e.g., Q-tube) or ultrasound irradiation technique as opposed to a traditional reflux system as described in the Example herein.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

Example

Summary

We synthesized dienaminone derivatives using ultrasound (US) and Q-tube techniques as performed by modern green chemistry techniques compared with the traditional reflux method. The prepared compounds were studied by IR, NMR, and MS. The anticancer effect of the compounds was also studied. The Q-tube and US techniques are environmentally friendly in that water waste and used energy are decreased due to the short reaction time.

Materials and Methods

General Method

All melting points were measured on a Gallenkamp Electrothermal melting points apparatus and was uncorrected. The Infrared spectra (KBr disks) in the range of 4000 to 400 $cm^{-1}$ was recorded on Perkin-Elmer Frontier™ spectrometer (USA). The second IR device is Spectrum Two™ FT-IR Spectrometer, detector type $LiTaO_3$, wavelength range 8300-350 $cm^{-1}$. The NMR spectra were recorded on 850 and 600 MHz NMR spectrometer deuterated in dimethylsulphoxide (DMSO-d6) and Chloroform deureated ($CDCl_3$). Chemical shifts are quoted in δ and were related to that of the solvent. Mass spectrum was carried out on direct probe controller inlet part to single quadropole mass analyzer in (Thermo Scientific GCMS) (Model ISQ LT) using Thermo X-Calibur™ Software at the regional center for mycology and biotechnology (RCMB) Al-Azhar University, NASER city, Cairo. X-ray crystallography was carried out on Kappa CCD Enraf Nonius FR 590 diffractometer, Kuwait. Ultrasound irradiation was carried out with a microprocessor controlled-2004, high intensity ultrasonic processor with temperature controller (750 W). The ultrasonic frequency of the cleaning bath used was equal to 25 KHz. The reaction temperature was manually input depending on the boiling point of solvent used and stabilized for more than an hour. Q-tube assisted reactions were performed in a Q-tube safe pressure reactor from Q Labtech, equipped with a cap/sleeve, pressure adapter (120 psi), needle, borosilicate glass tube, Teflon™ septum and catch bottle. Elemental analyses were performed using Perkin-Elmer™ 2400 Analyser. TLC Sigma-Aldrich™, Silica gel on TLC Al foils, silica gel matrix, with fluorescent indicator 254 nm.

General Procedure for Preparation of Dienaminone Derivative 2

A mixture of compound 1 (10 mmol) and DMFDMA (25 mmol) with little excess were refluxing at 90-100° C. overnight. The mixture was left at room temperature. The solid was collected by hexane and petroleum ether 40-60 then washed with ethanol. On the other hand, the same mixture was placed in Q-tube at 120° C./15 psi for 23-24 min. The products were collected and washed with ethanol.

2,6-Bis(3-dimethylamino-1-oxoprop-2-en-yl)pyridine (2)

Orange shine grain; (Q-tube)Yield 93.3%; m.p=236.4-237.2° C., FT-IR $v_{max}$ $cm^{-1}$: 3026,2911 (CH aromatic), 2807.2 (CH aliphatic), 1643.41 and 1628.84 (C═O ketone) (fingerprint area matched exactly with 2a(Δ)). $^1$HNMR (850 MHz, DMSO-d6): δ, ppm=2.961 (s, 6H), 3.201 (s, 6H), 6.549 (s, 2H broad alkene), 7.838-7.853 (d, 2H alkene), 8.012-8.074 (d, t, 3H, pyridine ring). One spot on TLC; eluent ($CHCl_3$:MeOH 85:15).

Reaction of dienaminone 2 with amino triazole and 2-amino-4,5,6,7-tetrahydrobenzo[b]thiophene-3-carbonitrile via Three Different Methods: Traditional(Δ), Q-Tube and US A mixture of compound 2 (10 mmol) and 4H-1,2,4-triazol-3-amine, or 2-amino-4,5,6,7-tetrahydrobenzo[b]thiophene-3-carbonitrile (25 mmol), in MeOH:$CH_3COOH$.glecial (1:1) were refluxing at 50-60° C. for 120 to 360 min. The solid was collected by filtration and washed with MeOH. Alternatively, a mixture was held at 120° C. for 10-20 min in Q-tube. Besides that, a mixture was placed in US at 60° C. for 30-60 min. Whether by Q-tube or US, the products were collected, washed, and crystallized in an appropriate solvent.

2,6-bis([1,2,4]triazolo[4,3-a]pyrimidin-7-yl)pyridine (4)

Brown crystal; (Δ) Yield 70.31%, (Q-tube) Yield 82.04% and (US) Yield 84.30%; 320-322° C., FT-IR $v_{max}$ $cm^{-1}$: 3061.95 (CH aromatic), 1962.48, 1842.35 (C═N) and 1609.30, 1567.13, 1538.73 (C═C aromatic). $^1$HNMR (850 MHz, DMSO-d6):δ, ppm=8.330 (d, 2H, pyrimidine), 9.218 (d, 2H, pyrimidine), 8.911 (s, 1H, triazole), 9.137 (d, 2H, pyridine), 8.530 (t, 1H, pyridine).

19, 2-(((Z)-3-(6-((E)-3-(dimethylamino)acryloyl) pyridin-2-yl)-3-oxoprop-1-en-1-yl)amino)-4,5,6,7-tetrahydrobenzo[b]thiophene-3-carbonitrile (6)

Brown crystal; (Δ)Yield 66.23%, (Q-tube) Yield 81.03% and (US)Yield 78.87%, FT-IR $v_{max}$ $cm^{-1}$: 3475.73 (NH str), 2937.12 (CH aromatic), 2211.33 (CN) 1736.4 (C═N) and 1536.42, 1593.02 (C═C aromatic) and 1630.86 (CO). $^1$HNMR (600 MHz, $CDCl_3$): δ, ppm=1.855-1.895 (m, 4H, $CH_2$), 2.612-2.654 (m, 4H, $CH_2$), 3.104, 3.268 (2s, 6H, $CH_3$), 6.612, 8.274 (s broad, 2H, CH alkene), 7.008 (d, J=7.846 Hz, 1H, CH alkene), 8.325 (d, J=7.66 Hz, 1H, CH alkene), 7.994 (t, 1H, pyridine) 7.401, 8.262 (dd, 2H, pyridine), 12.777 (d, 1H, NH). $^{13}$CNMR (150 MHz, $CDCl_3$): δ, ppm=190.6 (CO*2), 155.3 (CH), 152.9 (CH), 152.4 (C), 145.0 (C*2), 138.0 (CH), 134.3 (CH*2), 126.0 (C), 124.9 (C), 124.0 (C), 114.2 (CN), 96.2 (CH), 94.2 (CH), 37.7 (CH$_3$), 34.9 (CH$_3$), 24.6 (CH$_2$), 24.6 (CH$_2$), 23.3 (CH$_2$), 22.1 (CH$_2$). GC-MS: m/z calcd. for C$_{22}$H$_{22}$N$_4$O$_2$S 406.14, found 406.33 (M$^+$).

2,2'-(((1Z,1'Z)-pyridine-2,6-diylbis(3-oxoprop-1-ene-3,1-diyl))bis(azanediyl))bis(4,5,6,7-tetrahydrobenzo[b]thiophene-3-carbonitrile) (7)

Orange powder; (q)Yield 81.03% and (US)Yield 78.87%. FT-IR v$_{max}$ cm$^{-1}$: 2932.32, 2839.8 (CH aromatic), 2209.86 (CN) 1593.62, 1561.97 and 1521.04 (C=C aromatic) and 1621.78 (CO). $^1$HNMR (600 MHz, CDCl$_3$): δ, ppm=1.855-1.914 (m, 8H, CH$_2$ cyclo hexane), 2.623-2.668 (m, 8H, CH$_2$ cyclo hexane), 7.019, 7.032 (d, J=7.845 Hz 2H, CH alkene), 7.353-7.393 (dd, J=11.08 & 11.092, 2H, CH alkene), 8.037 (t, 1H, pyridine), 8.322, 8.335 (d, 2H, CH pyridine), 12.769, 12.788 (d, 2H, NH). $^{13}$CNMR (150 MHz, CDCl$_3$): δ, ppm=190.0 (CO*2), 153.4 (C*2), 152.4 (C*2), 145.2 (C*2), 138.4 (CH), 134.3 (CH*2), 126.1 (C*2), 124.8 (CH*2), 114.1 (CN*2), 96.1 (CH*2), 94.5 (C*2), 24.6 (CH$_2$*2), 24.6 (CH$_2$*2), 23.3 (CH$_2$*2), 22.1 (CH$_2$*2). GC-MS: m/z calcd. for C$_{29}$H$_{25}$N$_5$O$_2$S$_2$ 539.14, found 539.22 (M$^+$).

In Vitro Anticancer Activity

Cells suspended in medium (2×10$^4$ cells/mL) were plated in 96-well culture plates and incubated at 37° C. in a 5% CO$_2$ incubator. After 12 h, the test sample (2 μL) was added to the cells (2×10$^4$) in 96-well plates and cultured at 37° C. for 3 days. The cultured cells were mixed with 20 μL of MTT solution and incubated for 4 h at 37° C. The supernatant was carefully removed from each well and 100 μL of DMSO was added to each well to dissolve the formazan crystals which were formed by the cellular reduction of MTT. After mixing with a mechanical plate mixer, the absorbance of each well was measured by a microplate reader using a test wavelength of 570 nm. The results were expressed as the IC$_{50}$ (μM), which induces a 50% inhibition of cell growth of the treated cells when compared to the growth of control cells. Each experiment was performed at least 3 times. There was a good reproducibility between the replicate wells with standard error [46].

Cell Cycle Analysis and Apoptosis Detection

For cell cycle analysis, cell pellets were fixed with 70% ethanol on ice for 15 min and collected again. The collected pellets were incubated with propidium iodide (PI) staining solution (50 mg/mL PI, 0.1 mg/mL RNaseA, 0.05% Triton X-100) at room temperature for 1 hour and analyzed by Gallios® flow cytometer (Beckman Coulter, Brea, Calif., USA). Apoptosis detection was performed by FITC Annexin V/PI commercial kit (Becton Dickenson, Franklin Lakes, N.J., USA) following the manufacturer's protocol. The samples were analyzed by fluorescence-activated cell sorting (FACS) with a Gallios® flow cytometer (Beckman Coulter, Brea, Calif., USA) within 1 h after staining. Data were analyzed using Kaluzav® 1.2 (Beckman Coulter) [46].

Caspase-3 Assay

Activities of caspases-3 and -7 were measured using DRG Caspase-3 (human) ELISA (EIA-4860) kit (DRG International Inc., USA), Invitrogen. Caspase-7 (Active) (human) ELISA kit, Catalog #KHO1091 (96 tests) (Invitrogen Corporation, USA) according to the manufacturer's instructions.

Results

Dienaminone derivative 2 prepared by condensation of diacetyl compounds 1 with little excess of N,N-dimethylformamide dimethyl acetal (FIG. 1) by using reflux and high pressure reactor (Q-tube), observed high percentage of yield with short time preparation versus the traditional method [36,39]. An approximate percent of yield with microwave radiation method [38]. The comparative results between the two preparation methods is shown in Table 1.

TABLE 1

Time and yield of 2 by two synthesis methods

| | (Q-tube) | | (Δ) | |
|---|---|---|---|---|
| No. | Time(min) | Yield(%) | Time(min) | Yield(%) |
| 2 | 23 | 93.3 | 960 | 80 |

Identical JR and $^1$HNMR results approved in two methods used 2. The $^1$HNMR recorded 12H in δ range 2.900-3.201 ppm for 2 due to 2 NMe$_2$, two peaks broad single and doublet 4H for alkene at 6.549 and 7.854 ppm. Pyridine ring 3H shows two peaks doublet at 8.074 ppm and triplet at 8.012 ppm.

Figure 2:
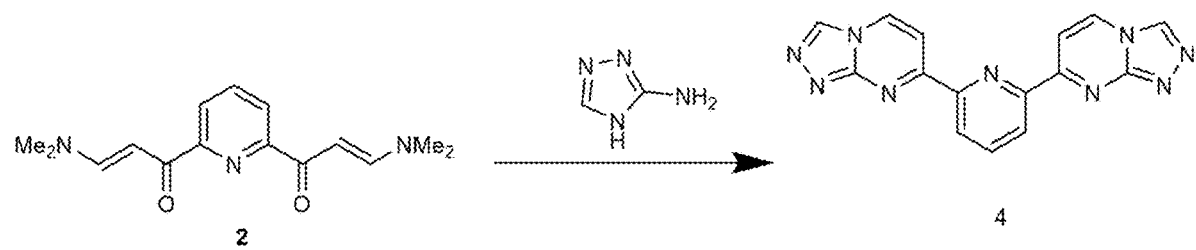
FIG. 2. Synthesis of compound 4.

Compound 2 considered as starting materials were reacted with 4H-1,2,4-triazol-3-amine (3) in methanol: glacial acetic acid 1:1 (FIG. 2) by the traditional method at 60° C., US at 60° C. and Q-tube at 120° C./30 psi to produce bis([1,2,4] triazolo[4,3-a]pyrimidin-7-yl) derivative 4. Compound 4 reported previously [40] with traditional method and recorded 60% of yield, during 480 to 720 min versus modern methods Q-tube and US recorded shorter reaction time and higher percentage yield Table 2.

TABLE 2

Time and yield of 4 by three synthesis methods

| | (Q-tube) | | (US) | | (Δ) | |
|---|---|---|---|---|---|---|
| No. | Time (min) | Yield (%) | Time(min) | Yield (%) | Time (min) | Yield (%) |
| 4 | 20 | 82.04 | 60 | 84.30 | 120 | 70.31 |

Figure 3:
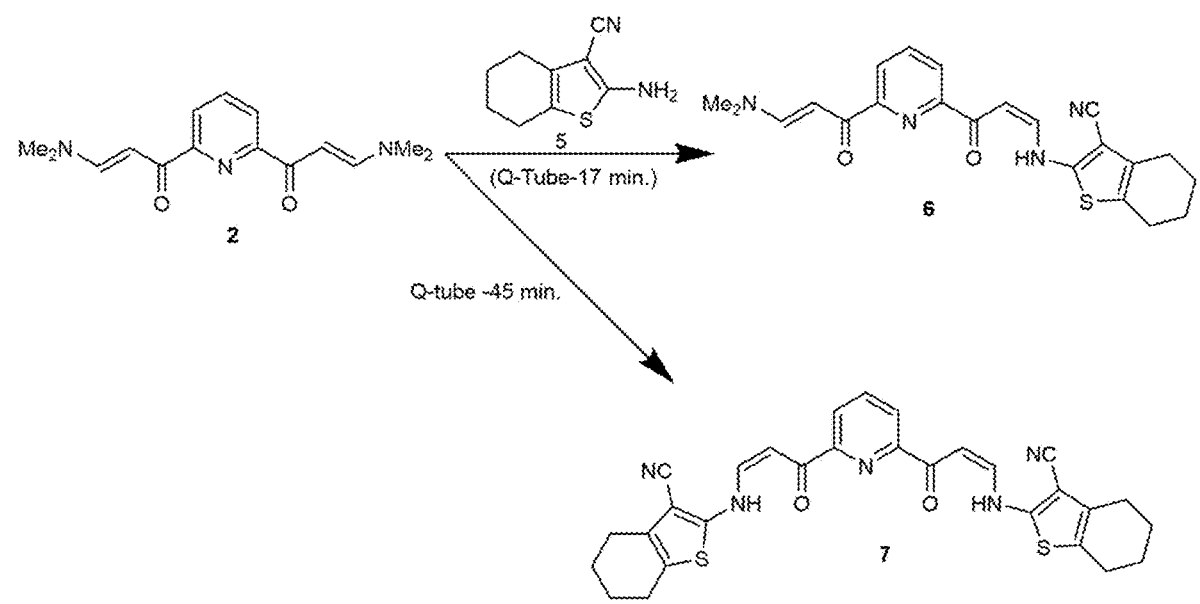
FIG. 3. Synthesis of compounds 6 and 7.

We extended our work to reaction of 2 with 2-amino-4,5,6,7-tetrahydrobenzo[b]thiophene-3-carbonitrile (5) in methanol: glacial acetic acid 1:1 (FIG. 3) by the traditional method at 60° C., US at 60° C. and Q-tube at 120° C./30 psi. It was found that in case of compounds 6 and 7, cyano group absorbance at 2200 cm$^{-1}$ in IR and 114 ppm in $^{13}$C NMR recorded. GC-MS: m/z was calculated for 6 406.14 and found 406.33 (M$^+$) and for 7 539.14 and found 539.22 (M$^+$). Table 3 below shows time and yield of three compounds by three different methods. There was a shorter preparation time for modern synthesis methods as compared to the traditional method (FIG. 3).

Reaction of 2 with 2-amino-4,5,6,7-tetrahydrobenzo[b] thiophene-3-carbonitrile in 17 min by Q-tube got two spots on TLC 6 and 7 while 45 min by Q-tube got one spot on TLC 7 confirmed by $^1$HNMR by disappearing methyl groups (table 3).

TABLE 3

Time and yield of 6 &7 by three synthesis methods

| | (Q-tube) | | (US) | | (Δ) | |
|---|---|---|---|---|---|---|
| No. | Time(min) | Yield(%) | Time(min) | Yield (%) | Time (min) | Yield (%) |
| 6 | 17 | 81.03 | 35 | 78.87 | 210 | 66.23 |
| 7 | 45 | 68.13 | — | — | — | — |

Figure 4:
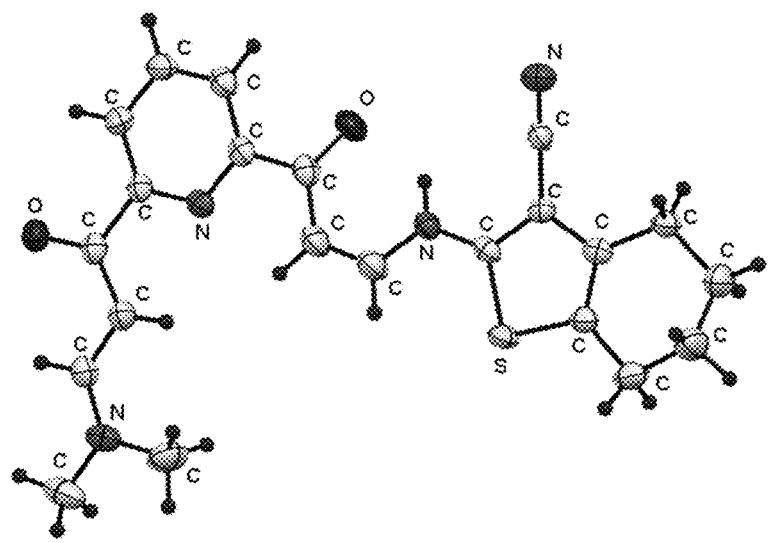
FIG. 4. 2-(((Z)-3-(6-(((E)-3-(dimethylamino)acryloyl)pyridin-2-yl)-3-oxoprop-1-en-1-yl)amino)-4,5,6,7-tetrahydrobenzo[b]thiophene-3-carbonitrile (6).

The x-ray of 2-(((Z)-3-(6-((E)-3-(dimethylamino)acryloyl)pyridin-2-yl)-3-oxoprop-1-en-1-yl)amino)-4,5,6,7-tetrahydrobenzo[b]thiophene-3-carbonitrile (6) is shown in FIG. 4.

In Vitro Anticancer Screening

In vitro cytotoxicity of the synthesized compounds 4, 6, and 7 was determined using the MTT assay against HL-60 (leukemia) cell lines. Doxorubicin (Doxo) one of the most efficient anticancer agentd was utilized as a reference compound in this study. The results are summarized in Table 4. According to MTT results, the compound displayed good cytotoxic activity and the activity is more pronounced in HL-60 cell line. Moreover, the most active compound 4 was tested against HL-60 at 50 μg/mL using Confluency analysis. The results showed that, cells appear as round, high-contrast objects in the image compared to healthy cells which show a normal adherent morphology [45].

TABLE 4

In vitro anticancer screening of the synthesized compounds 4, 6, and 7 against HL-60 human cance rcell lines.

| Compound code | $IC_{50}$ values (μg/mL) HL-60 |
| --- | --- |
| 4 | 3.28 ± 0.13 |
| 6 | 3.66 ± 0.11 |
| 7 | 28.54 ± 1.56 |
| Dox | 2.2 ± 0.08 |

Cell Cycle Analysis

Figure 5A:
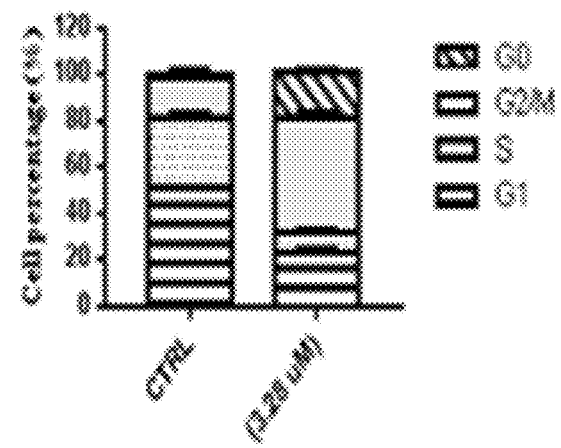
FIGS. 5A-B. A) Graphical representation of the cell cycle analysis of compound 4 at its $IC_{50}$ (μg/mL). B) Cell cycle analysis of compound 4 at its $IC_{50}$ (μg/mL).
Figure 5B:
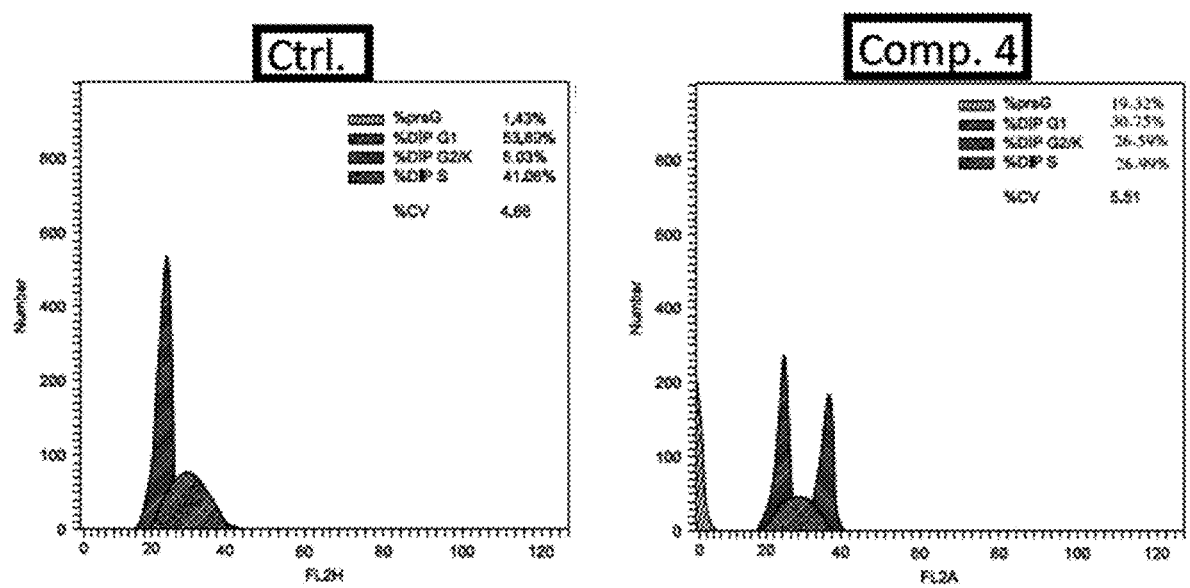

Cell cycle analysis was assessed in Leukemia HL-60 cell line after staining the nuclei with propidium iodide (PI) followed by DNA flow cytometry analysis. As illustrated in FIG. 5, exposure of Leukemia HL-60 cells to compound 4 at its $IC_{50}$ concentration showed interference with the normal cell cycle distribution profile of Leukemia HL-60 cell line. Compound 4 induced cell cycle arrest at G2/M phase as shown by marked increase of cell percentage in the G2/M phase from 16.80% to 51.84% compared with the untreated control. Additionally, compound 4 showed induction of apoptosis as revealed by increase in the percentage of cells at pre-G1 peak from 1.42% to 19.32% compared to control.

Annexin V-FITC/PI Apoptosis Detection of Compound 4

Figure 6A:
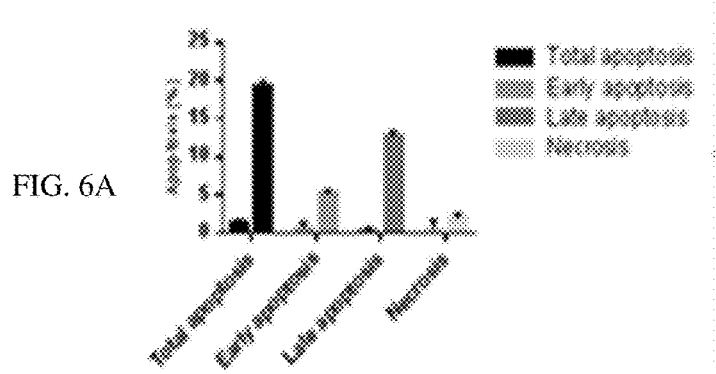
FIGS. 6A-B. A) Graphical representation of Annexin-V-PI analysis of compound 4. B) Annexin-V-PI analysis of compound 4.
Figure 6B:
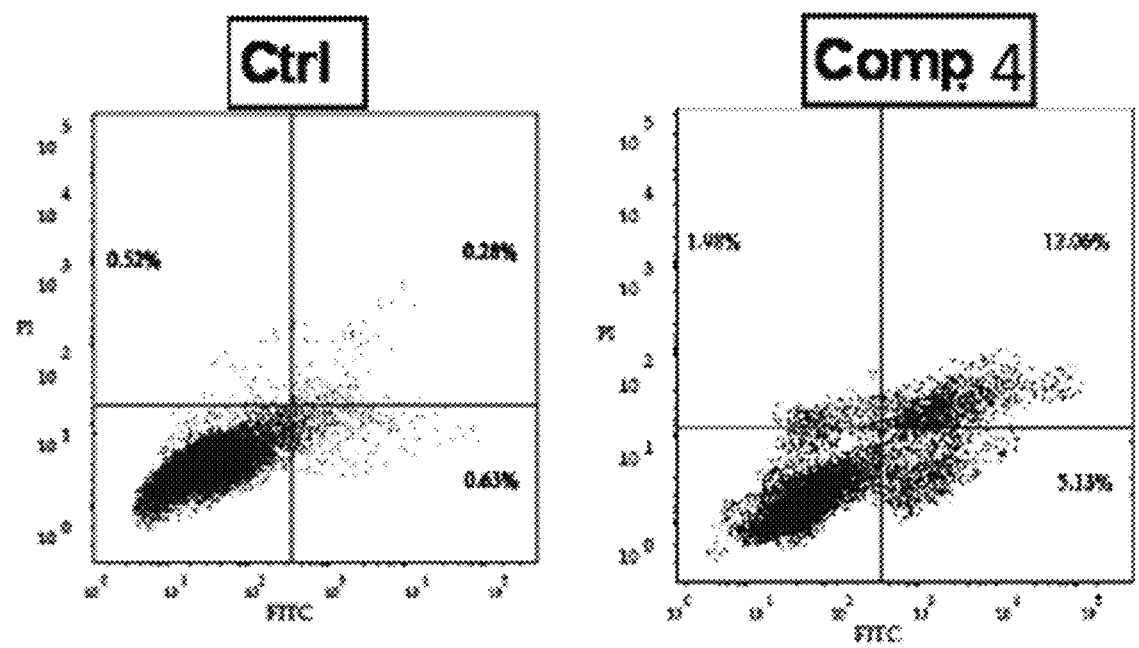

As shown in FIG. 6, the selected compound 4 showed a sharp decrease in the cell survival percentage in comparison with untreated control. Also, compound 4 increased the percentage of early apoptotic cells by 8.14-fold more than untreated control. Moreover, compound 4 increased the percentage of late apoptotic cells by 43.07-more than untreated control. The results suggested that compound 4 increased the apoptosis of Leukemia HL-60 cells.

Activated Caspase 3/7 Assay

Figure 7:
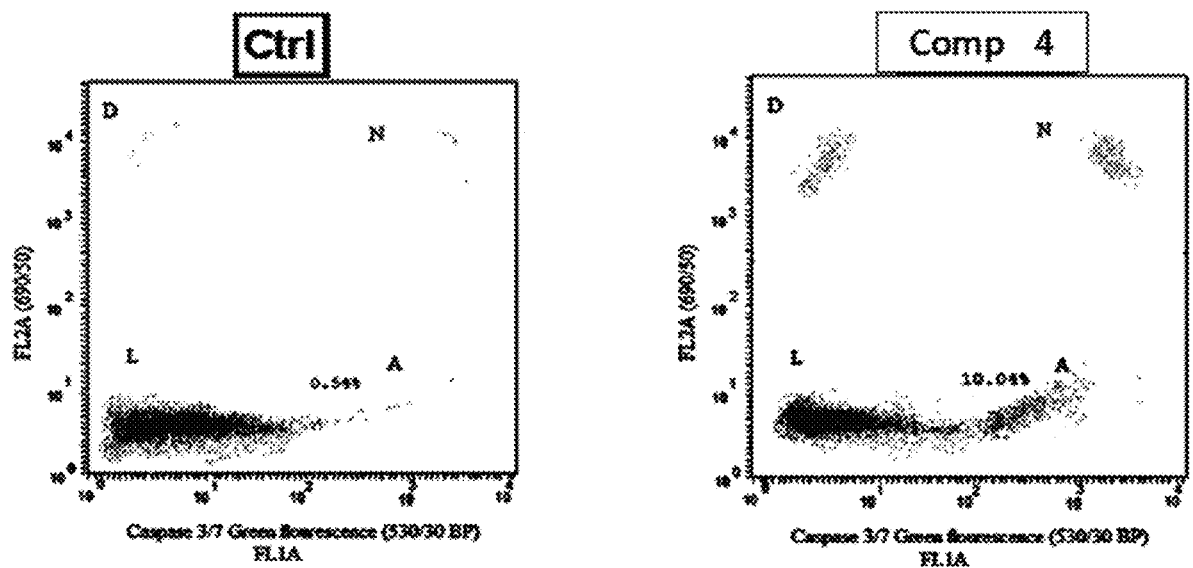
FIG. 7. Flow cytometric assay of caspase 3/7(%) of the tested compound 4 at its $IC_{50}$ (μg/mL).

The activation of caspase 3/7 was determined in compound 4 treated Leukemia HL-60 cells at $IC_{50}$ concentration using green flow cytometry assay for 24 h. The result in FIG. 7 showed an increase in the level of caspase 3/7 percentage from 0.54% to 10.04% compared with the untreated control. In conclusion, compound 4 can induce apoptosis in compound 4 treated Leukemia HL-60 cells and increase caspase 3/7 percentage higher than untreated control.

REFERENCES

1. Lin, J. P.; Yang, J. S.; Lin, J. J.; Lai, K. C.; Lu, H. F.; Ma, C. Y.; Sai-Chuen Wu, R.; Wu, K. C.; Chueh, F. S.; Gibson Wood, W.; Chung, J. G. Rutin inhibits human leukemia tumor growth in a murine xenograft model in vivo. *Envrion. Toxicol.,* 2012, 27(8), 480-484.
2. Lee, C. C.; Lin, C. N.; Jow, G. M. Cytotoxic and apoptotic effects of prenylflavonoid artonin B in human acute lymphoblastic leukemia cells. *Acta Pharmacol. Sin.,* 2006, 27(9), 1165-1174.
3. Zu, Y.; Liu, X.; Fu, Y.; Shi, X.; Wu, N.; Yao, L.; Efferth, T. Cytotoxic activity of isoliquiritigenin towards CCRF-CEM leukemia cells and its effect on DNA damage. *Planta Med.,* 2009, 75(10), 1134-1140.
4. Zhang, D.; Zhuang, Y.; Pan, J.; Wang, H.; Li, H.; Yu, Y.; Wang, D. Investigation of effects and mechanisms of total flavonoids of *Astragalus* and Calycosin on human erythroleukaemia cells. *Oxid. Med. Cell. Longev.,* 2012, 2012, 209843.
5. Zheng, J.; Hu, J. D.; Chen, Y. Y.; Chen, B. Y.; Huang, Y.; Zheng, Z. H.; Liu, T. B. Baicalin induces apoptosis in leukemia HL-60/ADR cells via possible down-regulation of the PI3K/Akt signaling pathway. *Asian. Pac. J. Cancer Prev.,* 2012, 13(4), 1119-1124.
6. Chang, H.; Lin, H.; Yi, L.; Zhu, J.; Zhou, Y.; Mi, M.; Zhang, Q. 3,6-Dihydroxyflavone induces apoptosis in leukemia HL-60 cell via reactive oxygen species-mediated p38 MAPK/JNK pathway. *Eur. J. Pharmacol.,* 2010, 648(1-3), 31-38.
7. Zhong, S.; Chen, Z.; Yu, X.; Chen, W.; Lv, M.; Ma, T.; Zhao, J. Tea consumption and leukemia risk: a meta-analysis. *Tumour Biol.,* 2014, 35(6), 5205-5212.
8. Deschler, B.; Lubbert, M. *Cancer,* 2006, 107, 2099-2107.
9. Alibhai S M, Leach M, Minden M D, Brandwein J. Outcomes and quality of care in acute myeloid leukemia over 40 years. *Cancer.* 2009; 115:2903-11.
10. Emadi A, Karp J E. The state of the union on treatment of acute myeloid leukemia. *Leukemia & lymphoma.* 2014; 55:2423-5.
11. Oran B, Weisdorf D J. Survival for older patients with acute myeloid leukemia: a population-based study. *Haematologica.* 2012; 97:1916-24.
12. Patel J P, Gonen M, Figueroa M E, Fernandez H, Sun Z, Racevskis J, Van Vlierberghe P, Dolgalev I, Thomas S, Aminova O, Huberman K, Cheng J, Viale A, Socci N D, Heguy A, Cherry A, Vance G, Higgins R R, Ketterling R P, Gallagher R E, Litzow M, van den Brink M R, Lazarus H M, Rowe J M, Luger S, Ferrando A, Paietta E, Tallman M S, Melnick A, Abdel-Wahab O, Levine R L. Prognostic relevance of integrated genetic profiling in acute myeloid leukemia. *The New England journal of medicine.* 2012; 366:1079-89.
13. Papaemmanuil E, Gerstung M, Bullinger L, Gaidzik V I, Paschka P, Roberts N D, Potter N E, Heuser M, Thol F, Bolli N, Gundem G, Van Loo P, Martincorena I, Ganly P, Mudie L, McLaren S, O'Meara S, Raine K, Jones D R, Teague J W, Butler A P, Greaves M F, Ganser A, Dohner K, Schlenk R F, Dohner H, Campbell P J. Genomic Classification and Prognosis in Acute Myeloid Leukemia. *The New England journal of medicine.* 2016; 374:2209-21.
14. Hole P S, Darley R L, Tonks A. Do reactive oxygen species play a role in myeloid leukemias? *Blood.* 2011; 117:5816-26.
15. Henry, G. D. *Tetrahedron,* 2004, 60, 6043.
16. Hirano, K.; Kubota, T.; Tsuda, M.; Mikami, Y.; Kobayashi, J. Pyrinodemins B-D, Potent Cytotoxic bis-Pyridine Alkaloids from Marine Sponge Amphimedon sp. *Chem. Pharm. Bull.,* 2000, 48, 974-977

17. Jacquemard, U.; Dias, N.; Lansiaux, L.; Bailly, C; Loge', C'd.; Robert, J. M.; Lozach, O.; Meijer, L.; Me'roura, J-Y.; Routiera, S. Synthesis of 3,5-bis(2-indolyl)pyridine and 3-[(2-indolyl)-5-phenyl]-pyridine derivatives as CDK inhibitors and cytotoxic agents, *Bioorganic & Medicinal Chemistry*, 2008, 16, 4932-4953.
18. Jabir N. R., Tabrez S., Ashraf G. M., Shakil S., Damanhouri G. A., Kamal M. A., *Int. J. Nanomed.*, 7, 4391-4408 (2012).
19. Desbene S., Giorgi-Renault S., *Curr. Med. Chem. Anticancer Agents*, 2, 71-90 (2002).
20. Mendelsohn B. A., Barnscher S. D., Snyder J. T., An Z., Dodd J. M., Chen H., Lin Z., Arnst K. E., Miller D. D., Li W., *Molecules*, 22, 1281 (2017).
21. Shi J., Mitchison T. J., Endocr. Relat. *Cancer*, 24, T83-T96 (2017).
22. Masawang K., Pedro M., Cidade H., Reis R. M., Neves M. P., Cor-rea A. G., Pinto M. M., *Toxicol. Lett.*, 229, 393-401 (2014).
23. Prota A. E., Danel F., Bachmann F., Bargsten K., Buey R. M., Pohl-mann J., Steinmetz M. O., *J. Mol. Biol.*, 426, 1848-1860 (2014).
24. Van Vuuren R. J., Visagie M. H., Theron A. E., Joubert A. M., *Can-cer Chemother. Pharmacol.*, 76, 1101-1112 (2015).
25. Dugal-Tessier J., *Bioconjug. Chem.*, 28, 371-381 (2017).
26. Gradishar W. J., *Breast Cancer, Basic a Clinical Research*, 6, 159-171 (2012).
27. Greene L. M., Nathwani S. M., Bright S. A., Fayne D., Croke A., Gagliardi M., O'Boyle N. M., *J. Pharmacol. Exp. Ther.*, 335, 302-313 (2010).
28. Zheng S., Zhong Q., Mottamal M., Zhang Q., Zhang C., Le Melle E., Wang G., J. Med. Chem., 57, 3369-3381 (2014).
29. Gaukroger K., Hadfield J. A., Lawrence N. J., Nolan S., McGown A. T., *Org. Biomol. Chem.*, 1, 3033-3037 (2003).
30. Schimmer A. D., *Cancer Res.*, 64, 7183-7190 (2004).
31. Chandele A., Prasad V., Jagtap J. C., Shukla R., Shastry P. R., *Neo-plasia*, 6, 29-40 (2004).
32. Carter B. Z., Milella M., Altieri D. C., Andreeff M., *Blood*, 97, 2784-2790 (2001).
33. Abadi A. H., Abouel-Ella D. A., Lehmann J., Tinsley H. N., Gary B. D., Piazza G. A., Abdel-Fattah M. A., *Eur. J. Med. Chem.*, 45, 90-97 (2010).
34. Abd elhameid, M. K.; Ryad, N.; Al-Shorbagy, M. Y.; Ismail, M. M.; El Meligie, S.
Design, Synthesis and Screening of 4,6-Diaryl Pyridine and Pyrimidine Derivatives as Potential Cytotoxic Molecules, *Chem. Pharm. Bull.* 66, 939-952 (2018).
35. Thapa, U.; Thapa, P.; Karki, R.; Yun, M.; Choi, J. H.; Jahnga, Y.; Lee, E.; Jeon, K-H.; Na, Y.; Ha, E-M.; Cho, W-J.; Kwon, Y.; Lee, E-S.; Synthesis of 2,4-diaryl chromenopyridines and evaluation of their topoisomerase I and II inhibitory activity, cytotoxicity, and structureeactivity relationship, *European Journal of Medicinal Chemistry*, 2011, 46, 3201-3209.
36. Lin, Y. I., & Lang Jr, S. A. Novel two step synthesis of pyrazoles and isoxazoles from aryl methyl ketones. *Journal Of Heterocyclic Chemistry*, 1977, 14(2), 345-347.
37. Bejan, E., Haddou, H. A., Daran, J. C., & Balavoine, G. G. A. The reaction of enaminones with carboxamidines: A convenient route for the synthesis of polyaza heterocycles. *Synthesis*, 1996, (08), 1012-1018.
38. Pleier, A. K., Glas, H., Grosche, M., Sirsch, P., & Thiel, W. R. Microwave assisted synthesis of 1-aryl-3-dimethylaminoprop-2-enones: a simple and rapid access to 3 (5)-arylpyrazoles. *Synthesis*, 2001, (01), 0055-0062.
39. Gamez, P., Steensma, R. H., Driessen, W. L., & Reedijk, J. (2002). Copper(II) compounds of the planar-tridentate ligand 2,6-bis(pyrazol-3-yl)pyridine. *Inorganica Chimica Acta*, 333(1), 51-56. https://doi.org/10.1016/S0020-1693(02)00754-5
40. Hassanien, A. Z. A. E. B. (2004). 2, 6-Bis [3-N, N-Dimethylamino-1-Oxopropen-1-Yl]Pyridine as a Building Block in Heterocyclic *Synthesis: Synthesis* of 2, 2': 6', 2"-Terpyridines and 2, 6-Bis [Pyrazolyl, Isoxazolyl, Diazepinyl, Pyrazolo [5, 1-a]Pyrimidinyl and Pyrazolo-[4, 3-D] Pyridazinyl] Pyridines. *Journal Of Chemical Research*, 2004(8), 536-540. https://doi.org/10.3184/0308234042563901
41. Moreira, D. N., Longhi, K., Frizzo, C. P., Bonacorso, H. G., Zanatta, N., & Martins, M. A. (2010). Ionic liquid promoted cyclocondensation reactions to the formation of isoxazoles, pyrazoles and pyrimidines. *Catalysis Communications*, 11(5), 476-479.
42. Shawali, A. S., & Haboub, A. J. (2011). Bis-enaminones as precursors for synthesis of novel 3,4-bis (heteroaryl) pyrazoles and 3, 6-bis-(heteroaryl)-pyrazolo [3, 4-d] pyridazines. *Journal of Chemical Research*, 35(6), 341-345.
43. El Azab, I. H., Break, L. M., & El-Zahrani, Z. A. (2016). Syntheses of Enaminone-Based Heterocyclic Compounds and Study their Biological Activity. *Oriental Journal Of Chemistry*, 32(5), 2435-2449.
44. Masaret, G. S. (2018). Convenient *Synthesis* of Polyaza-2-(heteroaryl) pyridine Derivatives. *Journal Of Heterocyclic Chemistry*, 55(3), 610-618.
45. Repetto, G., Del Peso, A., & Zurita, J. L. (2008). Neutral red uptake assay for the estimation of cell viability/cytotoxicity. *Nature protocols*, 3(7), 1125.
46. Hosamani K. M., Reddy, D. S., Devarajegowda, H. C. (2015) Microwave-assisted synthesis of new fluorinated coumarin-pyrimidine hybrids as potent anticancer agents, their DNA cleavage and X-ray crystal studies. *RSC Adv.* 5:11261-11271.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method for inducing apoptosis of cancer cells, comprising contacting the cancer cells with a compound having a chemical structure of Formula I

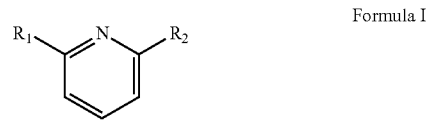

Formula I wherein $R_1$ is selected from the group consisting of

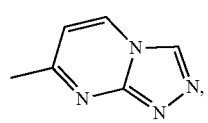

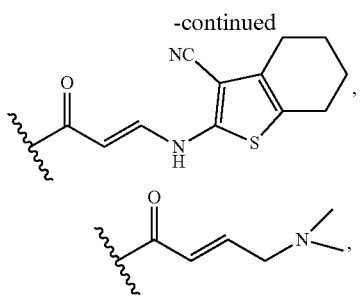

wherein $R_2$ is selected from the group consisting of

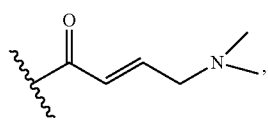

and where $R_1$ and $R_2$ are independently the same or different.

2. The method of claim 1, wherein the compound has a chemical structure of Formula II

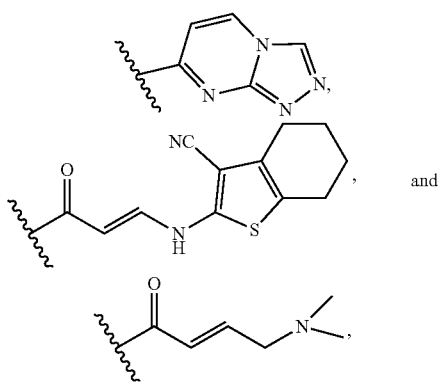

Formula II

3. The method of claim 1, wherein the compound has a chemical structure of Formula III

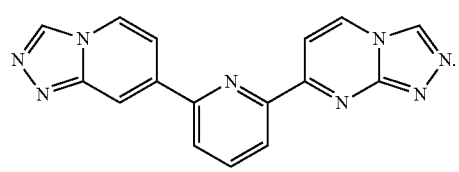

Formula III

4. The method of claim 1, wherein the compound has a chemical structure of Formula IV

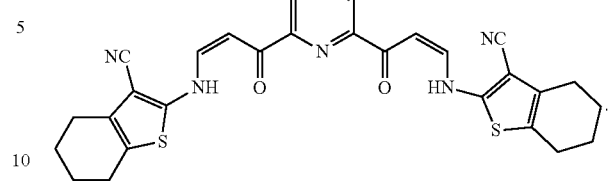

Formula IV

5. The method of claim 1, wherein the cancer cells are leukemia cells.

6. A compound of chemical structure of Formula I

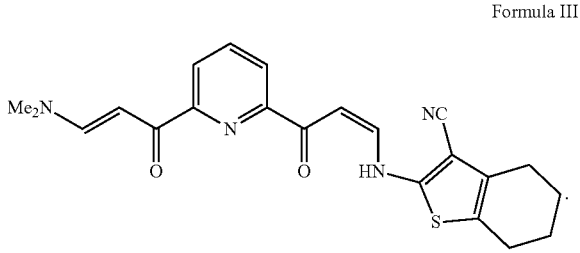 [SMILES: CN(C)/C=C/C(=O)c1cccc(C(=O)/C=C\Nc2sc3c(c2C#N)CCCC3)n1]

Formula I under conditions sufficient to cause apoptosis of cancer cells, wherein $R_1$ is selected from the group consisting of

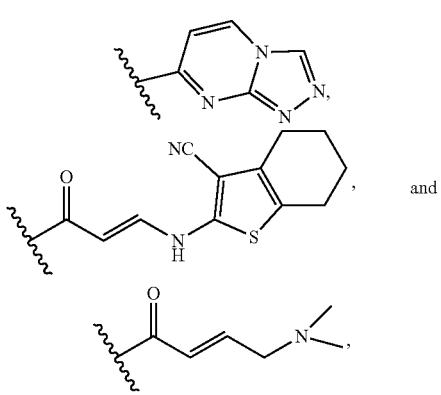

and wherein $R_2$ is selected from the group consisting of

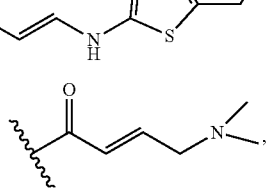

and where $R_1$ and $R_2$ are independently the same or different.

* * * * *